United States Patent [19]

Reichmann

[11] Patent Number: 5,015,794
[45] Date of Patent: May 14, 1991

[54] REDUCING XYLENE LOSS IN THE CATALYTIC ISOMERIZATION OF A XYLENE-CONTAINING FEED

[75] Inventor: Mark G. Reichmann, Oak Park, Ill.

[73] Assignee: Amoco Corporation, Chicago, Ill.

[21] Appl. No.: 410,665

[22] Filed: Sep. 21, 1989

[51] Int. Cl.$^5$ .......................... C07C 7/163; C07C 5/22
[52] U.S. Cl. ..................................... 585/258; 585/477; 585/481
[58] Field of Search ................ 585/253, 258, 477, 481

[56] References Cited

U.S. PATENT DOCUMENTS

| | | | |
|---|---|---|---|
| 3,448,039 | 6/1969 | Tarham | 585/258 |
| 4,118,429 | 10/1978 | Fitsch et al. | 585/258 |
| 4,654,456 | 3/1987 | Nimry | 585/477 |

Primary Examiner—Curtis R. Davis
Attorney, Agent, or Firm—Reed F. Riley; William H. Magidson; Ralph C. Medhurst

[57] ABSTRACT

Removal of the small amount of lower molecular weight olefins produced by certain isomerization catalysts during the catalytic isomerization of xylene results in reduced xylene loss. Such removal can be conveniently effected by use of a mild hydrogenation catalyst separate from the isomerization catalyst in the process.

6 Claims, 2 Drawing Sheets

REDUCING XYLENE LOSS IN THE CATALYTIC ISOMERIZATION OF A XYLENE-CONTAINING FEED

BACKGROUND OF THE INVENTION

This invention relates to reducing xylene loss in a continuous process for isomerizing a xylene-containing feed to a mixture rich in p-xylene in the presence of hydrogen over an isomerization catalyst which does not effectively reduce olefins produced during the isomerization process and, more particularly, relates to reducing xylene loss in a continuous process for isomerizing a xylene-containing feed to a mixture rich in p-xylene in the presence of hydrogen over a transalkylation-type of isomerization catalyst in which the small amount of low molecular weight olefinic hydrocarbons produced during isomerization are removed with a hydrogenation catalyst separate from the isomerization catalyst.

Typically, p-xylene is derived from mixtures of $C_8$ aromatics separated from such raw materials as petroleum naphthas, particularly reformates, usually by isomerization followed by, for example, lower-temperature crystallization of the paraxylene with recycle of the crystallizer liquid phase to the isomerizer. Principal raw materials are catalytically reformed naphthas and petroleum distillates. The fractions from these sources that contain the $C_8$ aromatics vary quite widely in composition but will usually contain 10 to 35 wt. % ethylbenzene and up to about 10 wt. % primarily $C_9$ paraffins and naphthenes with the remainder being primarily xylenes divided approximately 50 wt. % meta, and 25 wt. % each of the ortho and para isomers. The primarily $C_9$ paraffins and naphthenes can be removed substantially by extraction to produce what are termed "extracted" xylene feeds. Feeds that do not have the primarily $C_9$ paraffins and naphthenes removed by extraction are termed "unextracted" xylene feeds.

In the typical commercial process, isomerization of the xylene-containing feed takes place in the presence of hydrogen, and since little hydrogen is consumed in a once-through operation, a separation of the hydrogen and "light ends" is made after isomerization and returned to the isomerizer feed in the gas recycle stream.

Xylene isomerization catalysts can be classified into three types based upon the manner in which they convert ethylbenzene: (1) naphthene pool catalysts, (2) transalkylation catalysts, and (3) hydrodeethylation catalysts.

Naphthene pool catalysts are capable of converting a portion of the ethylbenzene to xylenes via naphthene intermediates. These catalysts contain a strong hydrogenation function, such as platinum, and an acid function, such as chlorided alumina, amorphous silica-alumina, or a molecular sieve. The role of the hydrogenation function in these catalysts is to hydrogenate the $C_8$ aromatics to establish essentially equilibrium between the $C_8$ aromatics and the $C_8$ cyclohexanes. The acid function interconverts ethylcyclohexane and the dimethylcyclohexanes via cyclopentane intermediates. These $C_8$ cycloparaffins form the so-called naphthene pool.

It is necessary to operate naphthene pool catalysts at conditions that allow the formation of a sizable naphthene pool to allow efficient conversion of ethylbenzene to xylenes. Unfortunately, naphthenes can crack on the acid function of the catalyst, and the rate of cracking increases with the size of the naphthene pool. Naphthene cracking leads to high xylene loss, and the byproducts produced by naphthene cracking are low-valued paraffins. Thus, naphthene pool catalysts are generally less economic than the transalkylation-type and hydrode-ethylation-type catalysts. Because of the strong hydrogenation character of this type of catalyst, any alkenes produced during isomerization would be reduced to alkanes.

The transalkylation catalysts generally contain a shape-selective molecular sieve. A shape-selective catalyst is one that prevents some reactions from occurring based on the size of the reactants, products, or intermediates involved. In the case of common transalkylation catalysts, the molecular sieve contains pores that are apparently large enough to allow ethyl transfer to occur via a dealkylation/realkylation mechanism, but small enough to substantially suppress methyl transfer which requires the formation of a bulky biphenylalkane intermediate. The ability of transalkylation catalyst to catalyze ethyl transfer while suppressing methyl transfer allows these catalysts to convert ethylbenzene while minimizing xylene loss via xylene disproportionation. The small amounts of lower alkenes such as ethylene, propylene, etc., produced during isomerization are not hydrogenated to alkanes and, they buildup in the system because they are recycled with the hydrogen in the recycle gas stream.

When ethyl transfer occurs primarily by dealkylation/realkylation, it is possible to intercept and hydrogenate the ethylene intermediate involved with this mechanism of ethyl transfer by adding a hydrogenation function to the catalyst. The primary route for converting ethylbenzene then becomes hydrodeethylation, which is the conversion of ethylbenzene to benzene and ethane. It is desirable to selectively hydrogenate the ethylene intermediate without hydrogenating aromatics (without establishing a naphthene pool) to prevent the cracking of the naphthenes that occurs over the acid function of the catalyst. Commercial hydrodeethylation catalysts selectively hydrogenate ethylene without substantial hydrogenation of aromatics at reported commercial conditions. At these same conditions, a small amount of certain impregnated metal compounds causes substantial hydrogenation of aromatics reducing the amount of p-xylene produced by the process.

In order to form a hydrodeethylation catalyst, it is essential to use an acidic component that behaves as a shape selective catalyst, i.e., one that suppresses the formation of the bulky biphenylalkane intermediate required for transmethylation, because transethylation can occur via a similar intermediate. For catalysts with pores large enough to allow the formation of these biphenylalkane intermediates, transethylation appears to occur primarily via these intermediates. In this case, ethylene is not an intermediate for transethylation, and the addition of a hydrogenation component cannot produce a hydrodeethylation catalyst.

When using a transalkylation-type isomerization catalyst in the typical commercial process, lower molecular weight olefins are produced in the isomerization and are returned to the isomerization reactor, after removal from the isomerization product, in the gas recycle stream where they can build up in the process. These lower molecular weight olefinic compounds, such as ethylene, propylene, and the like, can react with the xylene reducing the overall yield of p-xylene in the process. They can also lead to coke buildup on the isomerization catalyst which increases pressure drop in the reactor, decreases catalyst lifetime, and means the process temperature must be increased to maintain constant catalyst activity.

Now it has been found for xylene isomerization using a catalyst unable to substantially reduce the lower molecular weight olefins produced during isomerization, that use of a hydrogenation catalyst in the process to convert such olefins can substantially reduce the xylene loss leading to a greater overall p-xylene yield, and can also lead to lessen catalyst coking and longer catalyst lifetime.

BRIEF DESCRIPTION OF THE INVENTION

In one view the invention is the improvement in a continuous process for the isomerization over an isomerization catalyst in the presence of hydrogen of a xylene-containing feed, said isomerization producing a product rich in p-xylene and containing a small amount of lower alkenes, in which a hydrogenation catalyst separate from said isomerization catalyst is present to reduce xylene loss by removing said alkenes.

In another view the invention is the improvement in a continuous process for the isomerization over a molecular sieve-based, transalkylation-type of isomerization catalyst in the presence of hydrogen of a xylene-containing feed, said isomerization producing a product rich in p-xylene and containing a small amount of lower alkenes, in which a hydrogenation catalyst separate from said isomerization catalyst is present to reduce xylene loss by removing said alkenes.

DETAILED DESCRIPTION OF THE INVENTION

Figure 1:
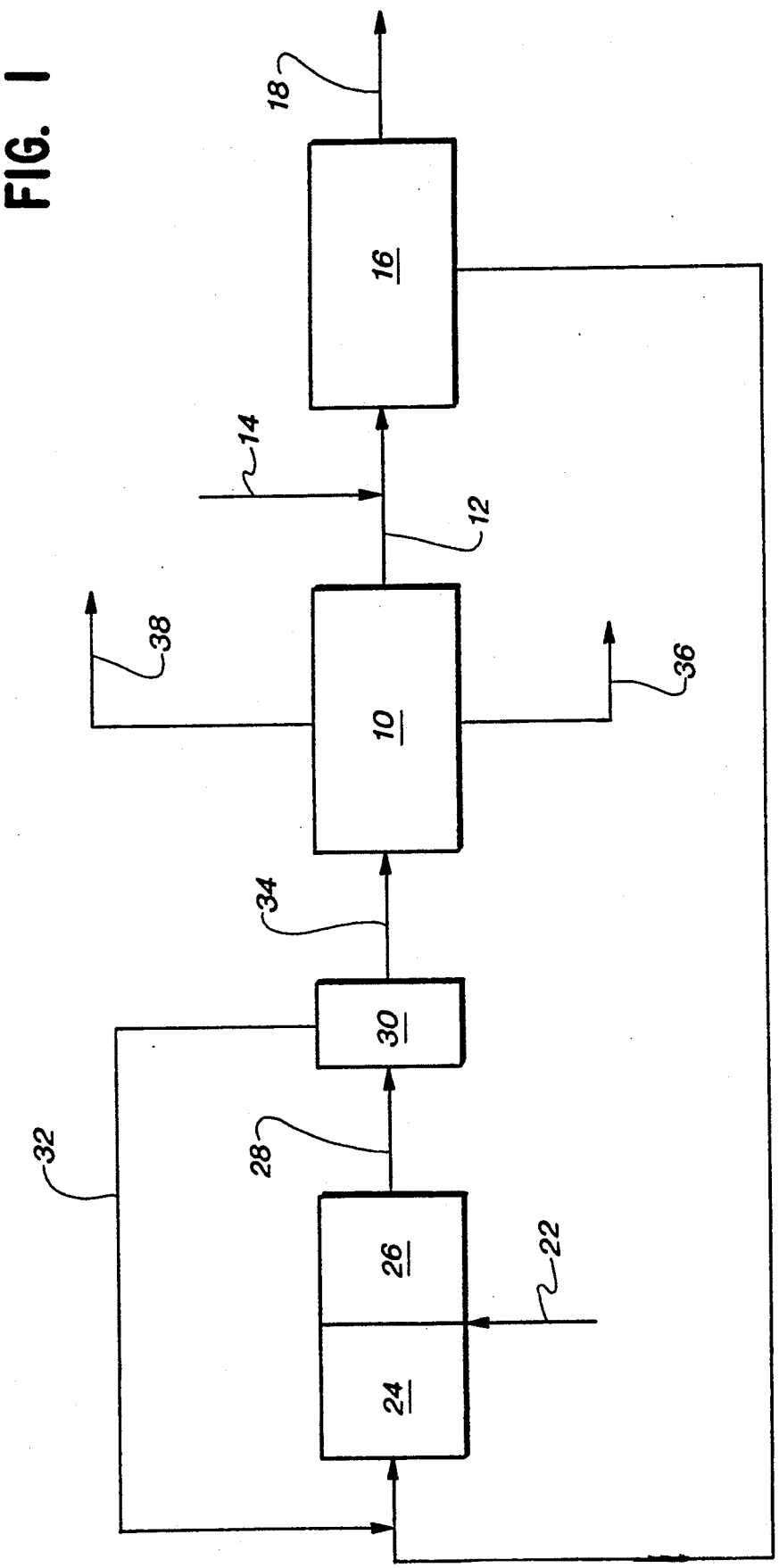
FIG. 1 shows a simplified flow diagram for one embodiment of a vapor phase, catalyzed xylene isomerization in which the hydrogenation catalyst and isomerization catalyst are layered in the isomerization reactor.
Figure 2:
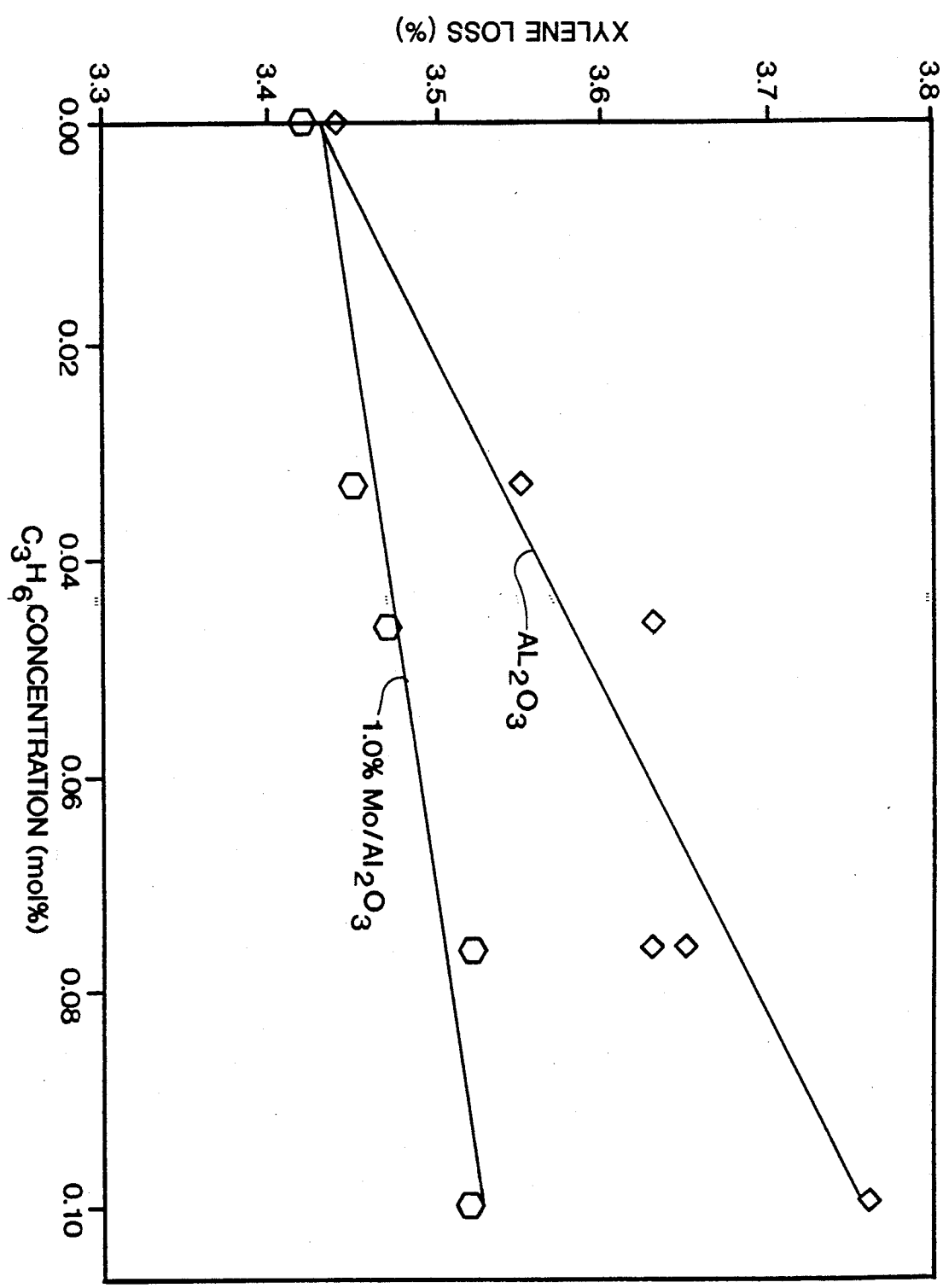
FIG. 2 shows a plot of xylene loss versus propylene concentration for a typical commercial xylene isomerization feed stream. The isomerization catalyst composition is a transalkylation-type, alumina-supported, HAMS-1B crystalline borosilicate molecular sieve. Curve 1 shows the xylene loss where the isomerization catalyst composition lies under an alumina bed, and Curve 2 shows xylene loss when the catalyst composition lies under a bed of 1 wt. % molybdenum on alumina. The xylene loss values are corrected to constant ethylbenzene conversion.

In the embodiment of the invention set out in FIG. 1, fresh mixed-xylene feed enters through line 14 and joins with separation section effluent exiting separation section 10 through line 12. The combined stream enters fractionation section 16 and is subject to low temperature crystallization. The p-xylene product exits through line 18 and the reject filtrate from fractionation section 16 is recycled to isomerization reactor 22 through line 20. Isomerization reactor 22 contains a bed containing hydrogenation catalyst 24 laid on top of isomerization catalyst 26. The isomerization product from isomerization reactor 22 exits through line 28 where the gaseous products including hydrogen and lower olefins are separated in separation section 30. These separated gaseous products are recycled through line 32 to the front end of isomerization reactor 22. The remainder of the product in separation section 30 is transferred via line 34 to separation section 10 where the heavy and light products are separated through lines 36 and 38, respectively.

The isomerization catalysts included in the invention described herein are those which produce olefins in the isomerization process but do not effectively eliminate them by conversion to a form which cannot react with xylene. Such catalysts can be of the transalkylation type, such as some of those based upon the ZSM series of aluminosilicate molecular sieves and those based on AMS-1B crystalline borosilicate molecular sieves. Preferred catalysts are catalyst compositions which employ a HAMS-1B, ZSM-5, ZSM-11, ZSM-22 and 23, ZSM-48, and the like sieve incorporated in an inorganic matrix such as alumina, silica-alumina, and silica, particularly alumina. Most preferred is HAMS-1B sieve incorporated in alumina. Such crystalline borosilicate molecular sieve catalyst compositions are taught in U.S. Pat. Nos. 4,268,420; 4,269,813; and 4,285,919, and Published European Patent No. 68,796.

The hydrogenation catalysts usefully employed herein include supported metal catalysts employing metals such as ruthenium, rhodium, nickel, cobalt, palladium, platinum, molybdenum, chromium or tungsten, more preferably, a supported metal such as cobalt, tungsten, chromium, molybdenum or nickel, and, most preferably, supported molybdenum. Support materials can be selected from among those materials commonly used for this purpose as can be understood by one skilled in the art, more preferably, silica, alumina, titania, zirconia and the like, and most preferably, alumina is used. A highly preferred hydrogenation catalyst is molybdenum on alumina. In choosing the hydrogenation catalyst, one must keep in mind that the catalyst must effectively reduce the lower olefins produced during isomerization but should be mild enough not to substantially reduce, crack or otherwise convert the xylene. The details of such hydrogenation catalysts including the wt. % of the supported metal are well-known to those skilled in the art. Although the amount of metal on the hydrogenation catalyst depends upon the particular act of reactor process conditions used, molybdenum on alumina catalysts generally involve use of a molybdenum content of between about 0.1 and about 5 wt. %.

The lower olefins produced by the isomerization catalysts included in this invention include, for example, ethylene, propylene, butenes, pentenes and the like. Their amounts, of course, depend upon the details on the particular isomerization catalyst and process used as may be understood by one skilled in the art.

The hydrogenation and isomerization catalysts are separate catalysts. While it is efficient to place the hydrogenation catalyst along with the isomerization catalyst in the isomerization reactor, it can be placed elsewhere in the isomerization process too, in particular, in the gas recycle loop in a separate hydrogenation reactor. In this case, a wider variety of hydrogenation catalysts can be used as the gas recycle stream contains no aromatics. If the hydrogenation catalyst is used in the isomerization reactor, it must be determined that the hydrogenation catalyst operates effectively at the process conditions used in the isomerization reactor. Also, the two types of catalysts should not react substantially if placed in intimate contact with each other when both are employed in the isomerization reactor.

When using both catalysts in the isomerization reactor, it is most effective to load the hydrogenation catalyst upstream of the isomerization catalyst. This can replace the guard bed of alumina which is often present in commercial xylene isomerization processes in the isomerization reactor.

It is believed that the ratio of volume of hydrogenation catalyst to volume of isomerization catalyst is not critical. However, too little hydrogenation catalyst may not keep the olefin concentration at a low enough level and too much hydrogenation catalyst may increase the xylene loss by hydrogenating and/or cracking xylene.

The application of this invention to benefit a xylene isomerization process necessarily entails operation at the conditions of such isomerization processes. The process details of such isomerization such as temperature, pressure, feed mol ratios, and space velocities are well known to those skilled in the art and are taught in U.S. Ser. No. 250,950, filed Sept. 29, 1988, now U.S. Pat. No. 4,885,427 as well as in numerous other patents such as U.S. Pat. No. 4,269,813, all of which are incorporated herein by reference.

While the invention is described for use in the typical vapor phase, fixed-bed xylene isomerization reactor, it can be employed in other process and reactor types such as a liquid-phase reactor as well.

The following Examples will serve to illustrate certain specific embodiments of the herein disclosed invention. These Examples should not, however, be construed as limiting the scope of the novel invention contained herein as there are many variations which may be made thereon without departing from the spirit of the disclosed invention, as those of skill in the art will recognize.

EXAMPLES

General

Reaction tests were conducted using a 2 ft stainless steel reactor with an i.d. of 0.5 in placed in a salt bath. The isomerization catalyst composition (40% HAMS-1B sieve supported on alumina) was loosely packed in the reactor with a guard bed resting on the leading edge of the catalyst with glass beads on either side. The Examples employ from 5 to 10 g of the isomerization catalyst and 5 g of guard bed with varying amounts of $Mo/Al_2O_3$ catalyst and alumina. Catalytic results were obtained at a temperature of about 680F., a pressure of 200 psig, a hydrogen to hydrocarbon mol ratio of 2.0 and a WHSV (with respect to the isomerization catalyst) of about 17 $hr^{-1}$. Olefin was introduced in the feed as a molar percentage of the total flow. Xylene loss was calculated from the difference between the weight percent xylene in the feed and product as determined by gas chromatography.

Example 1

The guard bed was prepared by adding 0.46 g of ammonium heptamolybdate to 50 g of distilled water. This solution was added to 50 g of Norton gamma-alumina in a glass bowl to the point of incipient wetness. The impregnated $Mo/Al_2O_3$ was then dried to 16 hr at 392F. and calcined for 4 hr at 900F. This results in a 0.5 wt % $Mo/Al_2O_3$ material.

Use of this guard bed is compared to use of an alumina guard bed for the case of a feed containing 0.1% propylene.

TABLE 1

| | Composition in Wt. % | | |
|---|---|---|---|
| Component | Feed | Effluent for $Al_2O_3$ Guard Bed | Effluent for 0.5% $Mo/Al_2O_3$ Guard Bed |
| Light paraffins | 0.000 | 0.095 | 0.075 |
| Benzene | 0.000 | 0.005 | 0.004 |
| Toluene | 0.004 | 0.925 | 0.715 |
| Para-Xylene | 99.913 | 23.702 | 23.955 |
| Meta-Xylene | 0.074 | 52.264 | 52.330 |
| Ortho-Xylene | 0.009 | 21.955 | 22.120 |
| Other | 0.000 | 1.054 | 0.801 |
| T (F) | | 682 | 683 |
| P (psig) | | 200 | 200 |
| $H_2$/HC | | 2.02 | 1.87 |
| WHSV | | 16.43 | 17.36 |
| % Xylene Loss | | 2.08 | 1.59 |

EXAMPLES 2 and 3

The guard bed was prepared by adding 1.84 g of ammonium heptamolybdate of 50 g of distilled water. This solution was added to 50 g of Norton Corp. gamma-alumina in a glass bowl to the point of incipient wetness. The impregnated $Mo/Al_2O_3$ was then dried 16 hr at 392F. and calcined 4 hr at 900F. This results in a 2.0 wt. % $Mo/Al_2O_3$.

Another guard bed was prepared by adding 2.76 g of ammonium heptamolybdate to 50 g of distilled water. This solution was added to 50 g of Norton Corp. gamma-alumina in a glass bowl to the point of incipient wetness. The impregnated $Mo/Al_2O_3$ was then dried 16 hr at 392F. and calcined 4 hr at 900F. This result in a 2.9 wt. % $Mo/Al_2O_3$.

Catalytic results from using these guard bed employing 0.1% propylene in the feed are shown in Table 2.

TABLE 2

| | Composition in Wt. % | | |
|---|---|---|---|
| Component | Feed | Effluent for 2.0% $Mo/Al_2O_3$ Guard Bed | Effluent for 2.9% $Mo/Al_2O_3$ Guard Bed |
| Light paraffins | 0.000 | 0.126 | 0.097 |
| Benzene | 0.000 | 0.009 | 0.005 |
| Toluene | 0.004 | 0.383 | 0.430 |
| Para-Xylene | 99.913 | 23.955 | 24.069 |
| Meta-Xylene | 0.074 | 52.858 | 52.653 |
| Ortho-Xylene | 0.009 | 22.226 | 22.264 |
| Other | 0.000 | 0.443 | 0.482 |
| T (F) | | 681 | 681 |
| P (psig) | | 200 | 200 |
| $H_2$/HC | | 2.03 | 1.94 |
| WHSV | | 16.66 | 17.28 |
| % Xylene Loss | | 0.96 | 1.01 |

EXAMPLE 4

The guard bed was prepared by adding 1.15 g of ammonium heptamolybdate to 50 g of distilled water. Forty grams of this solution was added to 50 g of Norton gamma-alumina in a glass bowl to the point of incipient wetness. The impregnated $Mo/Al_2O_3$ was then dried 16 hr at 392F. and calcined 4 hr at 900F. This results in a 1.0 wt. % $Mo/Al_2O_3$.

In Table 3 below, use of this guard bed is compared to use of an alumina bed for the case of 0.05% propylene in the feed.

TABLE 3

| Component | Feed | Effluent for Al$_2$O$_3$ Guard Bed | Effluent for 1.0% Mo/Al$_2$O$_3$ Guard Bed |
| --- | --- | --- | --- |
| Light P/N's | 0.004 | 0.224 | 0.227 |
| C$_9$ P/N's | 1.128 | 1.078 | 1.088 |
| Benzene | 0.358 | 2.262 | 2.286 |
| Toluene | 1.717 | 2.804 | 2.671 |
| Ethylbenzene | 13.945 | 10.615 | 10.656 |
| Para-Xylene | 8.027 | 18.028 | 18.073 |
| Meta-Xylene | 48.777 | 39.914 | 39.991 |
| Ortho-Xylene | 20.953 | 16.943 | 16.976 |
| Other | 5.091 | 8.132 | 8.032 |
| T (F) | | 680 | 681 |
| P (psig) | | 200 | 200 |
| H$_2$/HC | | 2.01 | 2.00 |
| WHSV | | 17.25 | 17.10 |
| Ethylbenzene Conversion, % | | 23.87 | 23.58 |
| % Xylene Loss | | 3.69 | 3.49 |

What is claimed is:

1. In a continuous process for the isomerization over an isomerization catalyst in the presence of hydrogen of a xylene-containing feed in a reactor, said isomerization producing a product rich in p-xylene and containing a small amount of lower alkenes, the improvement in which a hydrogenation catalyst separate from said isomerization catalyst is present in said reactor to reduce xylene loss by removing said alkenes.

2. In a continuous process for the isomerization over a molecular sieve-based, transalkylation-type, isomerization catalyst in the presence of hydrogen of a xylene-containing feed in a reactor, said isomerization producing a product rich in p-xylene and containing a small amount of lower alkenes, the improvement in which a hydrogenation catalyst separate from said isomerization catalyst is present in said reactor to reduce the xylene loss by removing said alkenes.

3. The process of claim 2 wherein said molecular sieve-based, transalkylation-type isomerization catalyst is a HAMS-1B crystalline borosilicate molecular sieve composited in an alumina matrix.

4. The process of claim 3 in which said hydrogenation catalyst comprises a minor amount of an element selected from the group consisting of Ru, Rh, Ni, Co, Rd, Pt, Mo, Cr and W composited in a major amount of an inorganic matrix.

5. The process of claim 2 wherein said hydrogenation catalyst contains a minor amount of molybdenum composited in a major amount of alumina.

6. The process of claim 5 wherein said minor amount of molybdenum lies between about 0.1 and about 5.0 wt. % of the total weight of said hydrogenation catalyst.

* * * * *